(12) United States Patent
van Dijk et al.

(10) Patent No.: US 9,354,158 B1
(45) Date of Patent: May 31, 2016

(54) DUCT AVERAGING SENSOR HAVING A CONNECTOR

(71) Applicant: Tasseron Sensors, Inc., Williamsport, PA (US)

(72) Inventors: Thomas J. van Dijk, Williamsport, PA (US); Kevin Alan Pool, Williamsport, PA (US)

(73) Assignee: Tasseron Sensors, Inc., Montoursville, PA (US)

( * ) Notice: Subject to any disclaimer, the term of this patent is extended or adjusted under 35 U.S.C. 154(b) by 544 days.

(21) Appl. No.: 13/745,794

(22) Filed: Jan. 19, 2013

Related U.S. Application Data

(60) Provisional application No. 61/589,063, filed on Jan. 20, 2012.

(51) Int. Cl.
| | |
|---|---|
| *G01D 11/24* | (2006.01) |
| *G01K 7/22* | (2006.01) |
| *H01R 43/26* | (2006.01) |
| *G01N 19/10* | (2006.01) |
| *B23P 19/00* | (2006.01) |
| *G01K 7/02* | (2006.01) |

(52) U.S. Cl.
CPC ............... *G01N 19/10* (2013.01); *B23P 19/00* (2013.01); *G01D 11/245* (2013.01); *G01K 7/02* (2013.01); *G01K 7/22* (2013.01); *H01R 43/26* (2013.01)

(58) Field of Classification Search
CPC ........... G01K 7/02; G01K 7/22; G01N 19/10; G01D 11/245; B23P 19/00; H01R 43/26
USPC ........................................................ 73/866.5
See application file for complete search history.

(56) References Cited

U.S. PATENT DOCUMENTS

| 2,147,021 | A | * | 2/1939 | Ford | G01K 5/326 |
| | | | | | 138/127 |
| 2,886,683 | A | * | 5/1959 | Klavitter | G01K 13/00 |
| | | | | | 338/229 |
| 3,186,227 | A | * | 6/1965 | Barlow | G01K 7/02 |
| | | | | | 136/233 |
| 3,319,215 | A | * | 5/1967 | Moore | G01K 7/023 |
| | | | | | 374/E7.005 |
| 3,356,980 | A | * | 12/1967 | Roberts | G01K 1/083 |
| | | | | | 338/22 R |
| 3,541,278 | A | * | 11/1970 | Roberts | G01K 1/083 |
| | | | | | 200/51.09 |
| RE27,354 | E | * | 5/1972 | Wiebe et al. | G01F 1/28 |
| | | | | | 374/142 |
| 4,386,525 | A | * | 6/1983 | Mooney | G01M 3/3245 |
| | | | | | 73/292 |
| 4,450,315 | A | * | 5/1984 | Waterman | G01K 1/08 |
| | | | | | 136/230 |
| 4,547,079 | A | * | 10/1985 | Alamprese | G01K 3/02 |
| | | | | | 374/116 |

(Continued)

OTHER PUBLICATIONS

Mamac Systems, Duct Temperature Sensors, Model TE-701/702 (2003), Minneapolis Minnesota.*

(Continued)

*Primary Examiner* — Lisa Caputo
*Assistant Examiner* — Punam Roy
(74) *Attorney, Agent, or Firm* — Robert J. Yarbrough; Lipton, Weinberger & Husick

(57) ABSTRACT

A duct averaging sensor has a plurality of sensor elements contained within a housing. A housing connector selectably joins the housing to a mating terminal connector. The terminal connector may be attached to the outside wall of a duct. The housing connector and terminal connector may be selectably attached and detached, with the housing extending into the inside of the duct. The selectable attachment of the housing to the terminal connector substantially eases installation and maintenance of the duct averaging sensor over prior art duct averaging sensors.

30 Claims, 13 Drawing Sheets

(56) References Cited

U.S. PATENT DOCUMENTS

| | | | | |
|---|---|---|---|---|
| 4,548,780 | A * | 10/1985 | Krohn | G01K 1/08 264/272.15 |
| 4,575,705 | A * | 3/1986 | Gotcher | G01K 13/02 338/229 |
| 4,959,633 | A * | 9/1990 | Kiraly | G01K 7/22 338/22 R |
| 5,056,048 | A * | 10/1991 | Seperant | G01K 7/25 374/170 |
| 5,167,153 | A * | 12/1992 | McQueen | G01F 1/684 338/22 R |
| 5,449,234 | A * | 9/1995 | Gipp | G01K 13/02 338/22 R |
| 6,267,010 | B1 * | 7/2001 | Hatanaka | G01D 11/245 374/E13.006 |
| 6,592,254 | B2 * | 7/2003 | Gul | 374/148 |
| 6,776,524 | B2 * | 8/2004 | Park | G01K 7/02 374/148 |
| 6,788,054 | B2 * | 9/2004 | Collins | G01D 11/245 324/174 |
| 6,890,095 | B2 * | 5/2005 | Gul | 374/148 |
| 7,021,354 | B2 * | 4/2006 | Kobayashi | G01D 11/245 123/203 |
| 7,201,513 | B2 * | 4/2007 | Nakabayashi | G01K 13/02 374/163 |
| 7,360,947 | B2 * | 4/2008 | Krishnamurthy | G01K 1/14 374/163 |
| 7,421,911 | B2 * | 9/2008 | Desrochers | G01N 1/26 374/141 |
| 7,447,607 | B2 * | 11/2008 | Schuh | G01K 15/00 374/E15.001 |
| 7,465,087 | B2 * | 12/2008 | Gul | 374/147 |
| 7,600,914 | B2 * | 10/2009 | Bronnert | G01K 7/16 374/163 |
| 7,656,269 | B2 * | 2/2010 | Mizoguchi | C01G 45/125 252/500 |
| 7,934,868 | B2 * | 5/2011 | Kubota | B01D 53/56 374/29 |
| 8,651,738 | B2 * | 2/2014 | Schlipf | H01R 13/405 374/100 |
| 2003/0024332 | A1 * | 2/2003 | Traphagen | G01D 11/245 73/866.5 |
| 2003/0063653 | A1 * | 4/2003 | Park | G01K 7/02 374/179 |
| 2003/0165181 | A1 * | 9/2003 | Gul | 374/185 |
| 2007/0127546 | A1 * | 6/2007 | Gul | 374/147 |
| 2007/0171959 | A1 * | 7/2007 | Irrgang | G01K 1/10 374/185 |
| 2007/0188163 | A1 * | 8/2007 | Jagiella | H03K 17/9505 324/207.15 |
| 2007/0240490 | A1 * | 10/2007 | Desrochers | G01N 1/26 73/31.01 |
| 2009/0211357 | A1 * | 8/2009 | Pinto | G01D 11/245 73/335.02 |
| 2009/0219705 | A1 * | 9/2009 | Glock | F02B 77/085 361/807 |
| 2010/0195694 | A1 * | 8/2010 | Claassen | G01K 17/10 374/29 |
| 2013/0177042 | A1 * | 7/2013 | Hermsen | A61L 2/28 374/179 |

OTHER PUBLICATIONS

Mamac Systems, Duct Averaging Temp Sensors, Model TE-705 (2003), Minneapolis Minnesota.*
Galvanizers Associated of Australia, "10 Real Benefits of Galvanized Steel", p. 1 (2011).*
DigiKey Electronics, On Shore Technology Inc. OSTTH060160, Term Block Plug, Accessed online on Jul. 20, 2015.*
DigiKey Electronics, On Shore Technology Inc. EDSTL130/06,Term Block Hdr, Accessed online on Jul. 20, 2015.*

* cited by examiner

DUCT AVERAGING SENSOR HAVING A CONNECTOR

I. RELATED APPLICATIONS

This application is entitled to priority from Provisional Patent Application 61/589,063 filed Jan. 20, 2012 by the inventors herein. Provisional Patent Application 61/589,063 is hereby incorporated by reference as if set forth in full herein.

II. BACKGROUND OF THE INVENTION

A. Field of the Invention

The present invention is directed to a duct averaging sensor for detecting an environmental condition of air within a duct. The duct averaging sensor is particularly suited to sensing the temperature of air as the air passes through the duct.

B. Statement of the Related Art

In a large heating, ventilation and air conditioning (HVAC) system, an air handling unit (AHU) may heat, cool, filter or humidify air to condition the air for the comfort of the occupants of a building. The AHU moves the conditioned air, known as supply air, through supply ducts and into the occupied spaces of the building. Return ducts transport return air from the occupied spaces back to the AHU. Makeup air from outside the building is mixed with the return air and the AHU conditions the combination of the return air and makeup air, completing the loop.

A control system is informed by sensors and controls the AHU. Sensors may be located within the return or supply ducts or both to monitor the return air and supply air. The control system may include other sensors as well. A sensor includes a sensor element and detects an environmental condition. As used in this document, the term 'environmental condition' means a characteristic of the air within the duct, for example: temperature, humidity and any other condition that may be useful to control the AHU. As used in this document, the term 'sensor element' refers to an apparatus capable of detecting an environmental condition at one location.

A sensor may utilize a single sensor element and detect an environmental condition at a single location within a duct. The weakness of a sensor utilizing a single sensor element is that the air in the duct may be stratified, with air at different locations in a cross section of the duct having different characteristics. Since the single sensor element can detect the environmental condition at only a single location, the single sensor element will provide the control system with incomplete information, resulting in poor control.

Duct averaging sensors address the shortcomings of sensors having a single sensor element by providing multiple sensor elements that detect the condition of the air at multiple locations within the duct. The multiple sensor elements are located in a single housing, which may be a length of tube. The multiple sensor elements are distributed along the length of the housing and detect the condition of the passing air at multiple locations along the length of the housing. For a large duct, the housing may be elongated, for example six, twelve or twenty-four feet in length, and may be a bendable tube composed of soft copper or aluminum. Such a duct averaging sensor features multiple sensor elements, for example, nine sensor elements. The multiple sensor elements are electrically connected to each other and terminate in a junction box permanently attached to one end of the tubing. As an alternative to a bendable housing, the housing may be straight and rigid.

In prior art duct averaging sensors, installation of the housing containing the sensor elements presents challenges to the installing technician, making proper installation a two-person job. As received by the technician, the bendable housing of a prior art duct averaging sensor is coiled and one end of the housing is permanently attached to the junction box. To install the prior art duct averaging sensor, a first technician drills a hole through the wall of the duct from the outside of the duct. The first technician then un-coils the coiled housing and passes the free end of the housing through the drilled hole from the outside of the duct to the inside of the duct. The first technician continues to pass the length of the housing through the hole until the junction box contacts the outside of the wall of the duct. A second technician located inside of the duct receives the free end of the housing and protects the housing as its entire length passes through the drilled hole and into the duct. The second technician arranges and secures the housing within the duct. The second technician arranges the bendable housing to locate the sensor elements to detect the condition of the air in the desired locations within the duct. The first technician attaches the junction box to the outside of the wall of the duct and connects the electrical leads of the duct averaging sensor to the control system. The electrical connections generally are made using screw terminals, wire nuts or solder.

The step of passing the entire length of the housing through the drilled hole presents a hazard of flexing or kinking the housing. Flexing or kinking the housing can damage the sensors, wires or connections contained within the housing. An apparatus for quickly and reliably installing a duct averaging sensor is needed.

III. SUMMARY OF THE INVENTION

The invention is a duct averaging sensor that includes a mating pair of housing connectors and terminal connectors configured to join sensor elements located inside a duct to terminals mounted on the outside wall of the duct. The mating terminal connector and housing connector can be selectably connected and disconnected. The terminals are configured for connection to a control system. The advantage of the mating connectors is that the terminals and the housing can be separately installed and separately maintained, which substantially eases the tasks of installing, replacing and servicing the duct averaging sensor over prior art duct averaging sensors.

The sensor elements are contained within a housing. The housing may be a tube, such as a bendable tube composed of copper or aluminum. The sensor elements are distributed along the length of the tube. A sensor element for determining temperature may utilize any of the technologies known in the art, including, for example and without limitation, a thermister, a thermocouple or a resistance temperature detector. A sensor element for determining humidity may include any of the technologies known in the art, including for example and without limitation, a capacitive humidity sensor, a resistive humidity sensor or a thermal conductivity humidity sensor. Any other sensor and any combination of sensors for any environmental condition is contemplated by the invention. The sensor elements are electrically joined together and to a housing connector. The housing connector is attached to one end of the housing and is configured to matably connect to the terminal connector.

The terminal connector is configured to be attached to the outside wall of the duct and to communicate with the inside of the duct through a hole defined by the outside wall. The terminal connector may be mounted directly to the outside wall of the duct with the terminals exposed. Alternatively, the terminals may be enclosed to protect the terminals and the connection to the control system from damage. An enclosure may be defined by the terminal connector, as, for example, a molded enclosure. Alternatively, the terminal connector may be enclosed within a conventional junction box, as a junction box composed of galvanized steel.

The electrical connection between the housing connector and the terminal connector join electrical leads connected to the sensing elements to the terminals and may be any configuration known in the art. Two probes attached to the terminal connector engaging two conductive apertures defined by the housing connector have proven successful in practice. The sensor elements within the housing are connected together and define a single electrical circuit when connected to the control system through two electrical leads; however, connection of any number of electrical leads defining any number of circuits for a single pair of mating connectors is contemplated by the invention.

The mechanical connection between the terminal connector and the housing connector comprises a male portion defined by the housing connector and a female portion defined by the terminal connector. The male and female portions join in a sliding fit, the orientation of which may be controlled by a key and corresponding slot defined by the male and female portions. A locking nut having female threads is rotatably retained on the housing connector by a boss. The female threads of the locking nut are configured to engage male threads defined by the outside of the terminal connector, retaining the housing connector to the terminal connector.

The sliding fit of the housing connector and terminal connector, coupled with the locking nut, provides a robust mechanical connection between the housing and the terminal connector to provide reliable operation and a long service life for the duct averaging sensor. Any other fastening mechanism known in the art can be used to retain the housing connector to the terminal connector, including without limitation: a bayonet connection, an interference fit, an adhesive connection, a threaded connection utilizing screws, bolts or nuts to attach the housing and terminal connectors, a connection using mechanical clips, or any other connection by which the housing connector may be releasably attached to the terminal connector. When connected, the mating housing and terminal connectors are water tight and exclude air, water, dust and water vapor, thereby protecting the electrical connection between the sensor elements and the terminals.

Terminals for connection to a control system are attached to the terminal connector and may be enclosed within a junction box or other enclosure, including an enclosure defined by the terminal connector. The junction box may be configured to be mounted to the outside of the wall of the duct, as by flanges attached to the junction box and having holes to receive sheet metal screws. Any other means known in the art to connect the terminal connector, junction box or enclosure to the outside of the wall of the duct is contemplated by the invention, including without limitation screws, bolts, clips, threads, adhesive and hook-and-loop fasteners. The terminal connector is disposed on a back side of any enclosure or junction box and is configured to communicate through a prepared hole in the wall of the duct.

Spring clips define the electrical terminals inside the junction box, although any other mechanism to make an electrical connection is contemplated by the invention. Wire leads from the control system may be clipped to the spring clips, avoiding the use of wire nuts, solder joints, spade connectors, threaded nuts, electrical tape or other electrical attachments. Any holes communicating through the junction box to transmit wire leads from the control system may be equipped with resilient grommets or strain reliefs during manufacture so that the technician is not required to perform the step of installing a grommet or strain relief during installation.

To install the duct averaging sensor having a terminal connector without an enclosure or junction box, the technician will drill a hole in the wall of the duct in the desired location. The technician will insert the terminal connector through the hole and will secure the terminal connector to the outside of the wall of the duct, as by sheet metal screws passing through flanges defined by the terminal connector. The technician will enter the interior of the duct and will attach the housing connector to the terminal connector, thereby attaching the housing to the junction box both mechanically and electrically. For a housing in the form of a bendable tube that is received by the technician in the coiled condition, the technician will uncoil the tube and will dispose the tube within the interior of the duct so that the sensor elements will detect the environmental condition, for example temperature, at the desired locations within the duct. The technician will connect the terminals of the terminal connector to electrical leads from the control system, completing installation. The duct averaging sensor is then ready to use. Only one technician is required for installation and the technician does not pass the elongated housing through the drilled hole in the wall of the duct, avoiding a hazard to the housing and its contained wiring and sensor elements.

To install the duct averaging sensor of the invention having an enclosure defined by the terminal connector or where the terminals of the terminal connector are enclosed within a junction box, the technician fill follow the steps of the immediately preceding paragraph, with the added steps that the technician will pass the electrical leads of the control system through a grommet or strain relief in a hole communicating to the interior of the enclosure or junction box prior to connecting the lead to the terminals. The technician also will install the enclosure or junction box cover, enclosing the terminals.

The terminal connector may be equipped with clips, a nut, or any other suitable connections to secure the terminal connector within a knock-out of a conventional junction box. The technician may then enclose the terminals within the conventional junction box at the time of installing the duct averaging sensor within the duct.

Should the duct averaging sensor require replacement, the technician can enter the duct and release the housing connector from the terminal connector. The technician can replace the housing and attach the housing connector of the new housing to the existing terminal connector. Only one technician is required and the technician is not required to disturb the terminals or the control lead from the control system to the terminals.

IV. BRIEF DESCRIPTION OF THE DRAWINGS

V. DETAILED DESCRIPTION OF AN EMBODIMENT

Figure 1:
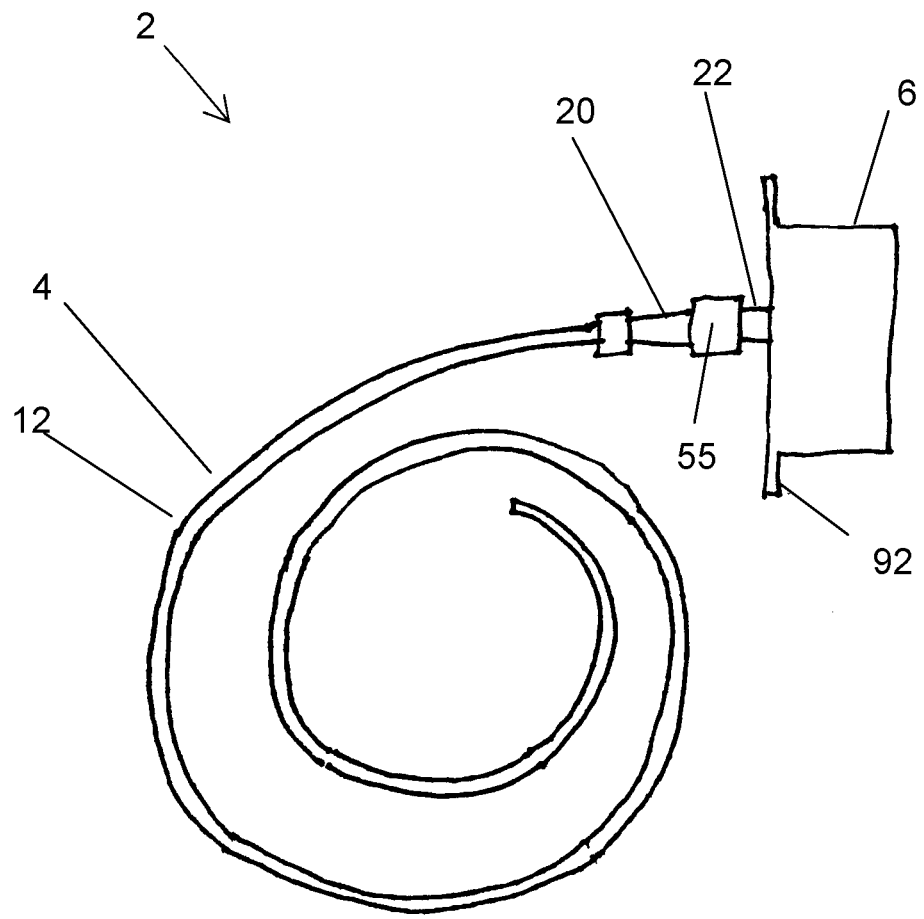
FIG. 1 is a side view of the duct averaging sensor of the invention with the housing coiled and with the housing attached to the junction box.
Figure 2:
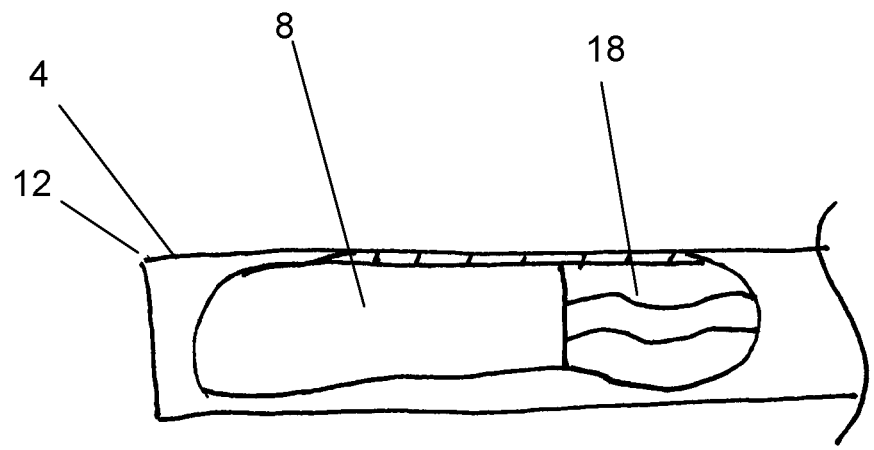
FIG. 2 is a detailed cutaway view of the housing showing a sensor element.
Figure 3:
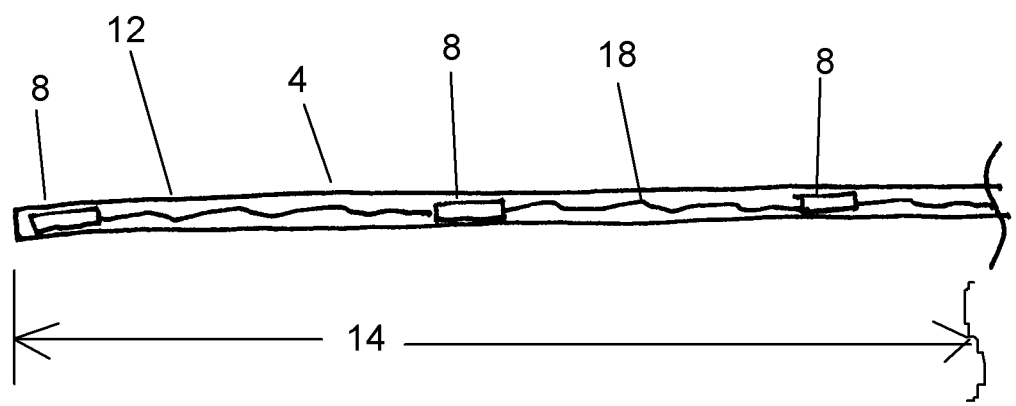
FIG. 3 is a detail cutaway view of the housing showing three sensor elements.

As shown by FIGS. 1, 2 and 3, the invention is a duct averaging sensor 2. The duct averaging sensor has a housing 4 and a terminal connector 22. In FIG. 1, the terminals 26 (shown by FIGS. 5 and 7) of the terminal connector 22 are enclosed within a junction box 6. The housing 4 contains a plurality of sensor elements 8. Each sensor element 8 is configured to detect an environmental condition within a duct 10. The housing 4 may be an elongated tube 12. Tube 12 may be composed of a bendable material, such as copper or aluminum. As received by a technician for installation, a housing 4 may be coiled, as shown by FIG. 1. Housing 4 is uncoiled and arranged within a duct 10 during the installation process, as described below.

As shown by FIG. 3, housing 4 has a length 14. The plurality of sensor elements 8 are distributed along the length 14 of the housing 4 and each sensor element 8 is configured to detect the environmental condition of the air (indicated by arrow 16 on FIG. 5) moving past the sensor element 8. From FIGS. 2 and 3, the sensor elements are electrically connected by sensor leads 18.

Figure 4:
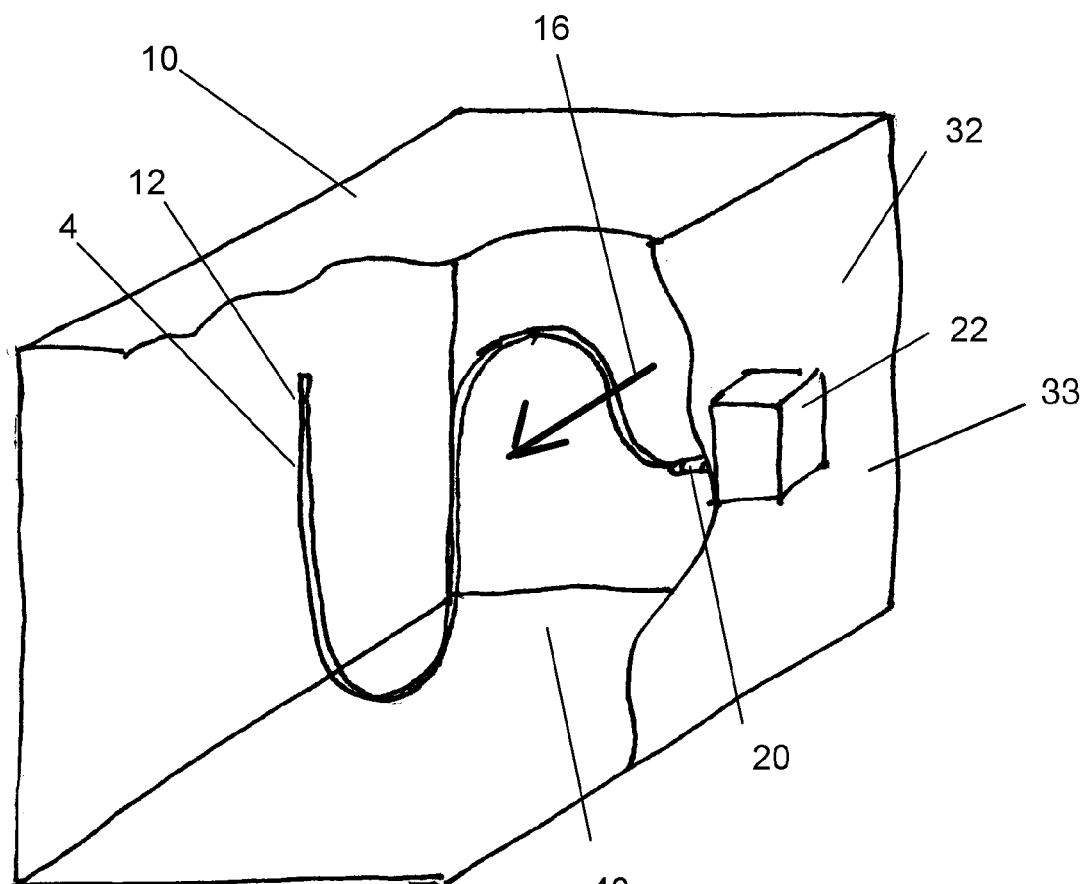
FIG. 4 is a perspective cutaway view of the terminal connector and housing installed in a duct with one arrangement of the housing within the duct.

The housing 4 is selectably attached by a housing connector 20 to a terminal connector 22. In FIG. 4, the terminal connector 22 is attached to the outer surface 33 of the outside wall 32 of the duct 10 and shows that the housing 4 disposed inside 40 the duct 10. Housing 4 is shown in FIG. 4 in one possible arrangement to monitor air 16, indicated by the arrow, moving through the duct 10.

Figure 5:
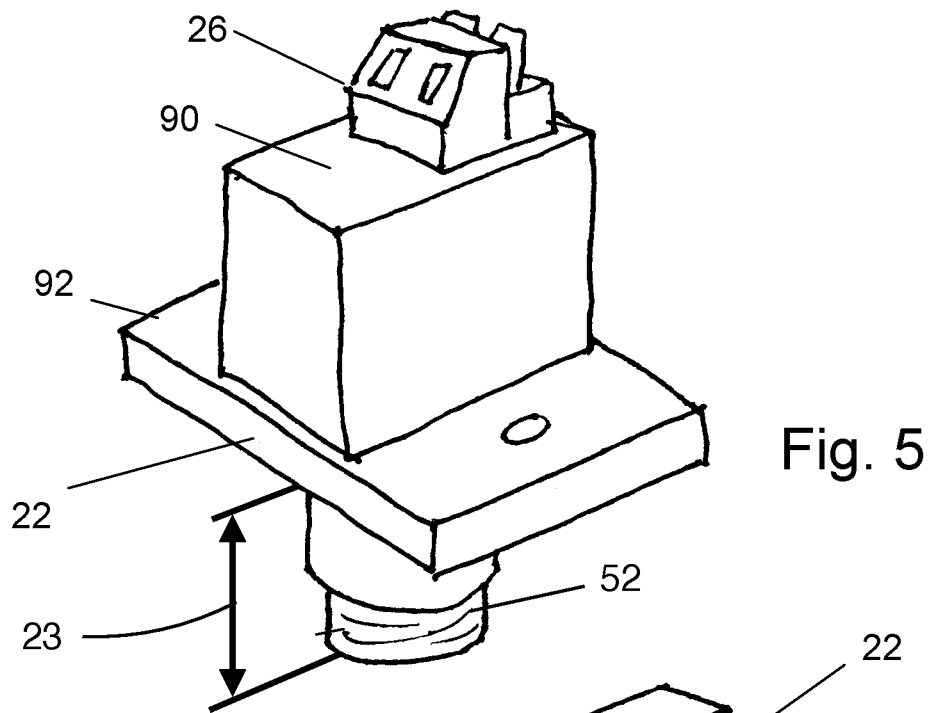
FIG. 5 is a first perspective view of a molded flange connector.
Figure 6:
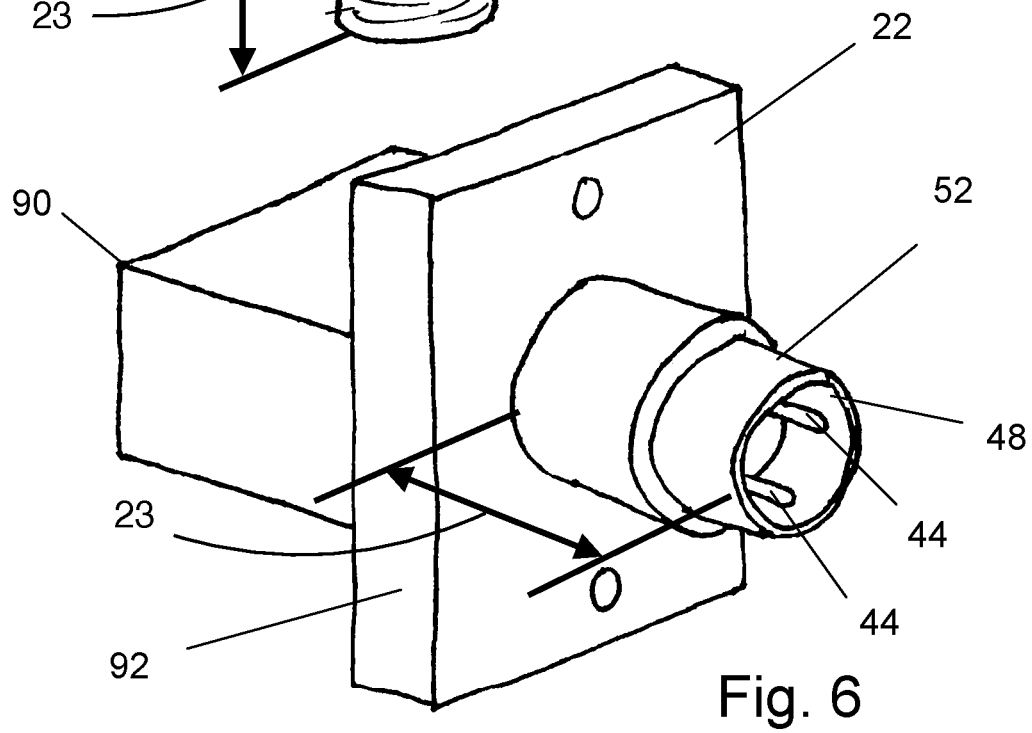
FIG. 6 is a second perspective view of a molded flange connector.
Figure 7:
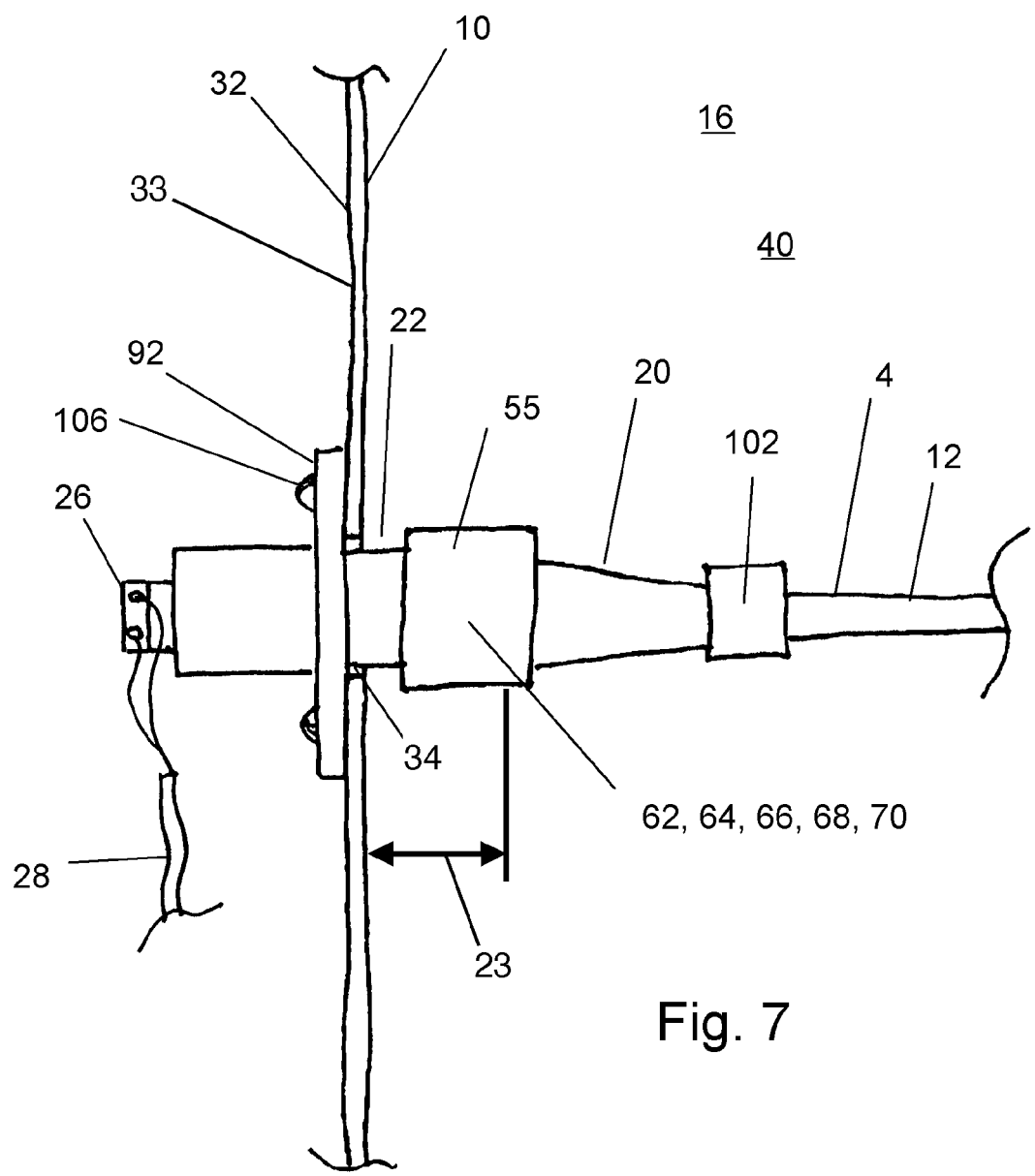
FIG. 7 is a cutaway side view of a molded flange connector installed in a duct.

A terminal connector 22 in this instance a molded flange connector 90, is shown by FIGS. 5, 6 and 7. The terminal connector 22 defines a terminal connector length 23. A flange 92 allows the terminal connector 22 to be attached to the outer surface 33 of the outside wall 32 of the duct 10, shown by FIG. 7. From FIG. 7, duct 10 defines an outside wall 32 and outside surface 33. A hole 34 communicates through the outside wall 32 to the inside 40 of the duct 10. The terminal connector 22 is disposed in the hole 34 and the terminal connector length 23 communicates through hole 34. Flange 92 is attached to the outer surface 33 of the outside wall 32, supporting the terminal connector 22 on the duct 10. The housing connector 20 is releasably attached to the terminal connector 22 and the housing 4, which may be a tube 12, is attached to the housing connector 20 on the inside 40 of the duct 10. The housing 4 may be attached to the housing connector by a compression fitting 102. The housing connector 20 may attach to the terminal connector 22 by any fastening mechanism known in the art.

From FIG. 7, the terminals 26 of the terminal connector 22 are located outside of the duct 10 when the terminal connector 22 is installed. The terminals 26 are connected to control leads 28, which carry the electrical signal generated by the sensor elements 8 to the control system 30. For the molded flange connector 90 illustrated by FIGS. 5-7, no enclosure is provided and in use the terminals 26 are exposed to the environment outside the duct 10. The terminals 26 preferably are configured for quick connection, such as spring-loaded terminals 26.

Figure 8:
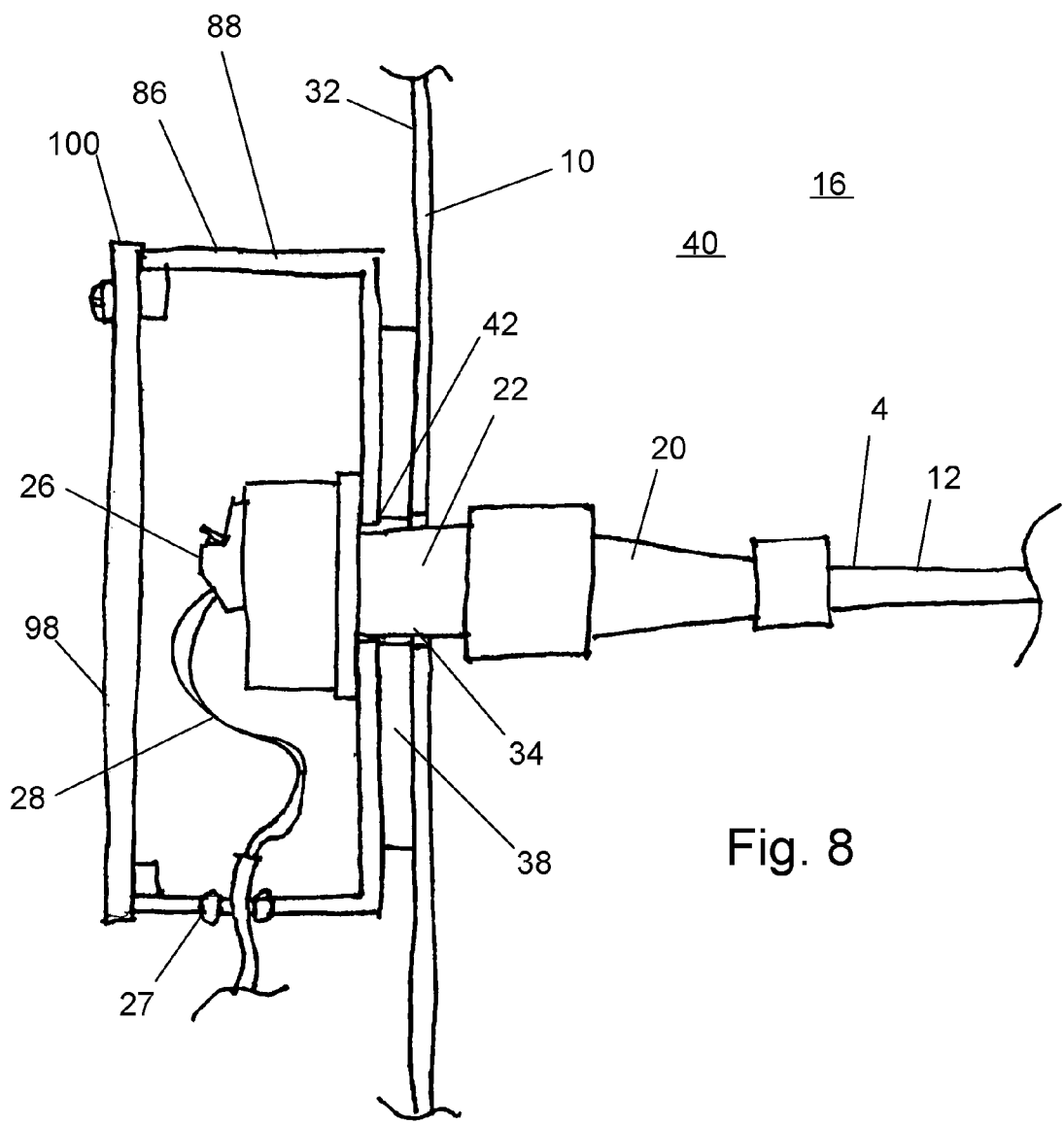
FIG. 8 is a cutaway side view of a galvanized enclosure connector installed in a duct.

FIG. 8 illustrates a molded flange connector 90 (shown by FIGS. 5-7) attached to a junction box 6, such as a galvanized steel junction box 86, to define a galvanized flange connector 88. The galvanized steel junction box 86 is attached to the outside wall 32 of the duct 10 to locate the terminal connector 22. The housing connector 20 is subsequently attached to the terminal connector 22 from inside 40 the duct 10. The galvanized steel junction box 86 is closed with a cover 98, protecting the connectors 26 and the connection of the control leads 28 to the connectors. The junction box 6 defines an opening through which the control lead 28 passes. A strain relief 27 is disposed in the hole and also helps exclude dust.

Figure 9:
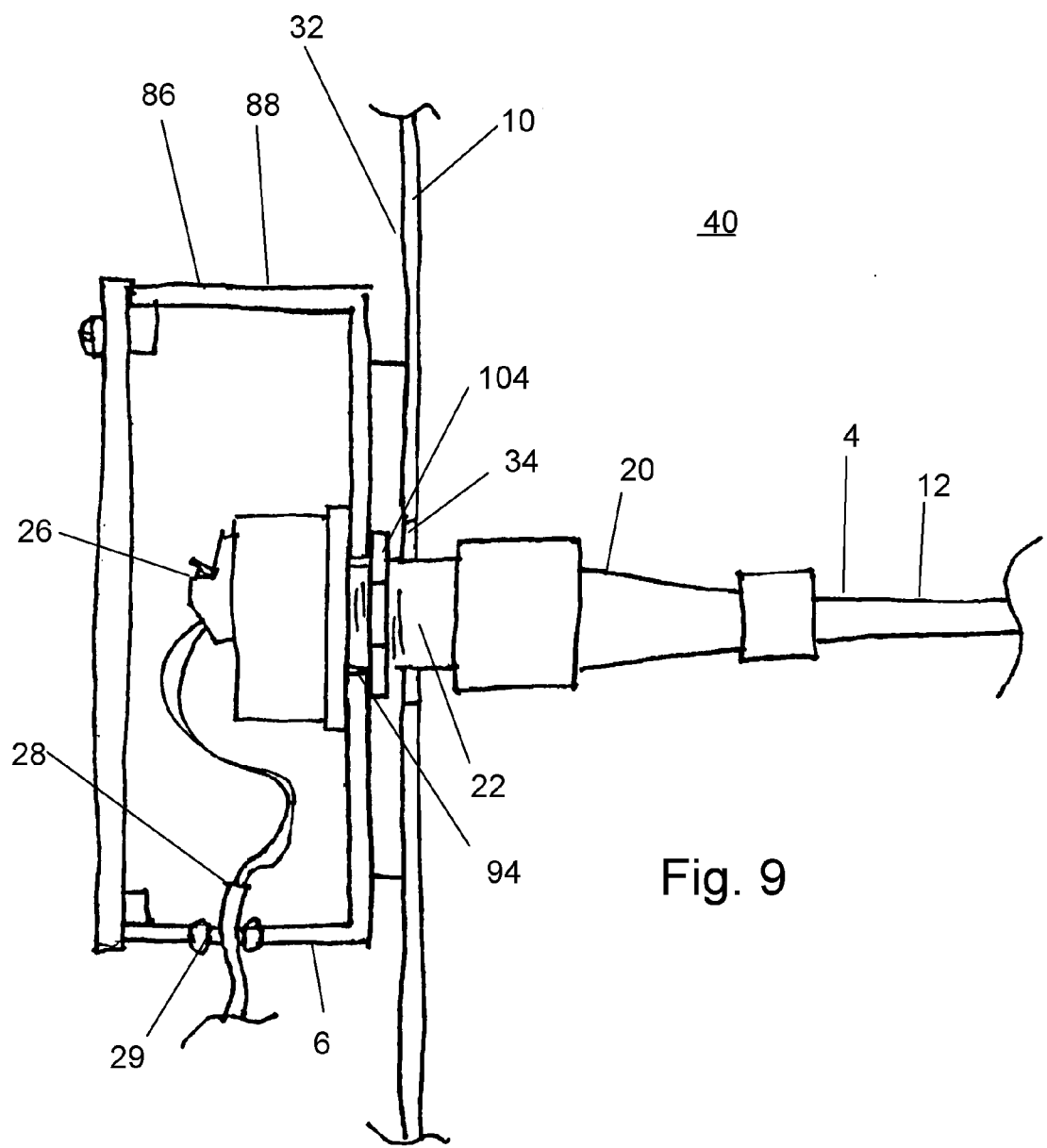
FIG. 9 is a cutaway side view of a molded flange connector installed in knock-out opening of a junction box and installed in a duct.

FIG. 9 illustrates an alternative embodiment of the terminal connector 22 configured to allow a technician to install the terminal connector 22 in a conventional junction box 6 at the time of installation of the duct averaging sensor 2. The technician removes a conventional knock-out to reveal a knock-out opening 94. The technician then passes the terminal connector 22 through the knock out opening 94 and secures the terminal connector 22 in the knock-out opening 94. In the illustration of FIG. 9, a nut 104 secures the terminal connector 22 to the junction box 6; however, any attachment known in the art may be used to retain the terminal connector 22 in the knock-out opening 94, including without limitation screws, bolts, clips, threads, clamps, adhesive and hook-and-loop fasteners. To install the terminal connector 22 to the duct 10, the technician aligns the terminal connector 22 with the hole 34 and attaches the junction box 6 to the outside wall of the duct 10, as by passing sheet metal screws through flanges 92 on the junction box 6, shown by FIG. 1.

Figure 10:
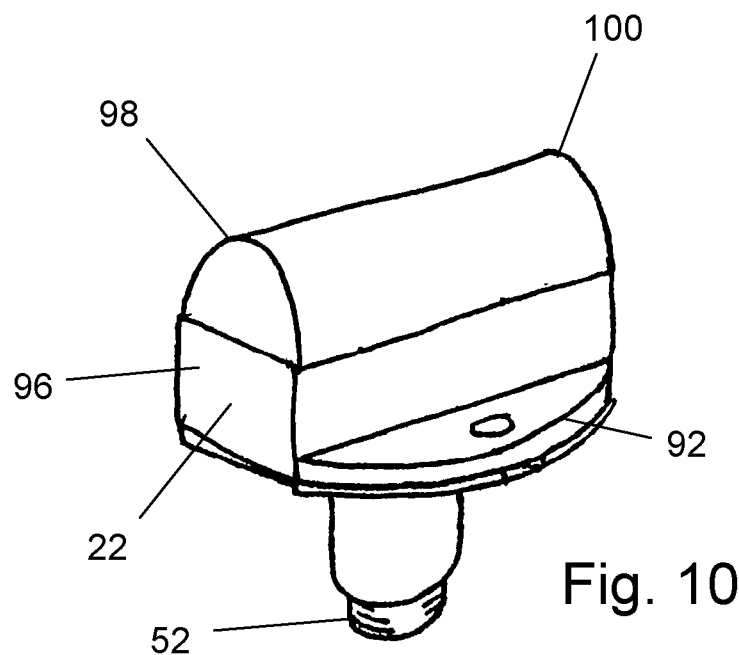
FIG. 10 is a first perspective view of a molded enclosure connector.
Figure 11:
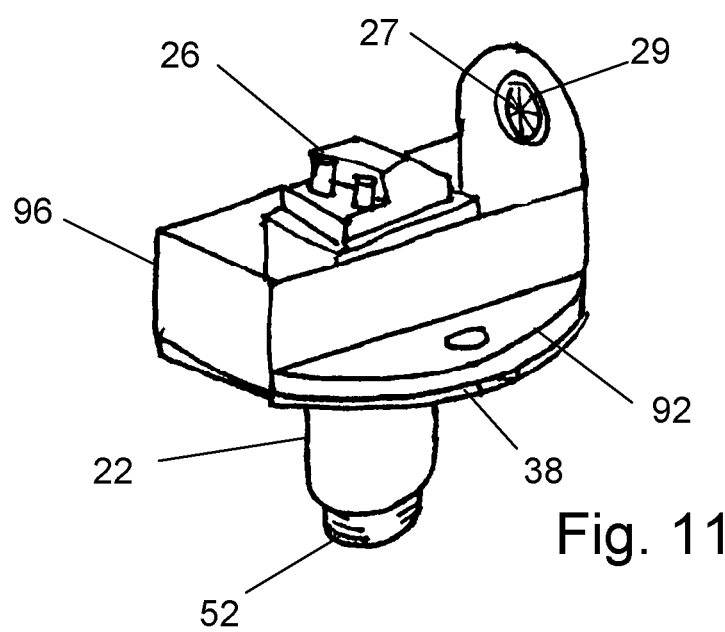
FIG. 11 is a second perspective view of a molded enclosure connector with the cover removed.
Figure 12:
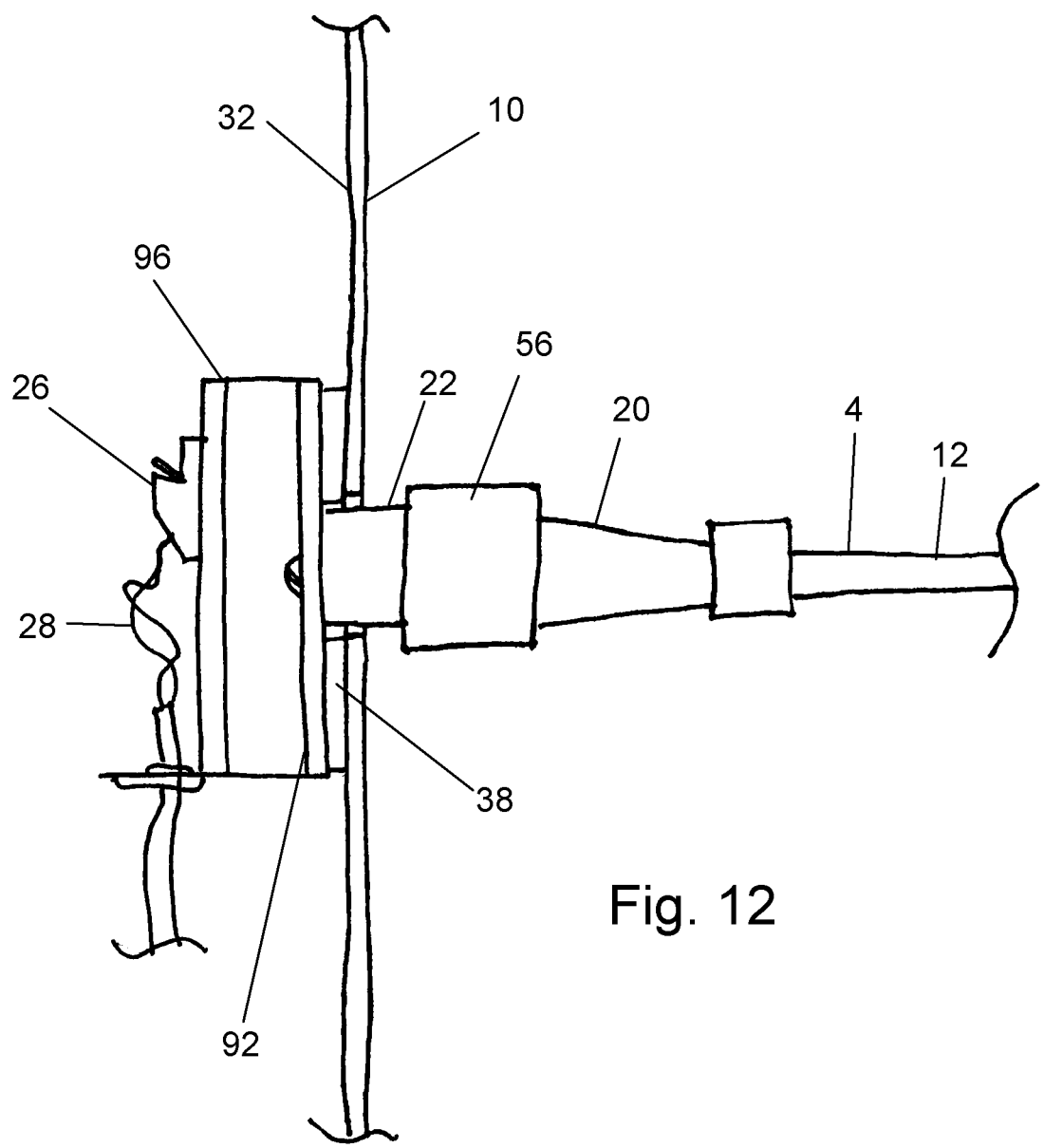
FIG. 12 is a cutaway side view of the molded enclosure connector installed in a duct, with the cover removed.

FIGS. 10, 11 and 12 illustrate an alternative embodiment in which the terminal connector 22 defines a base 96. The combination of the base 96 and a cover 98 define an enclosure 100 that protects the terminals 26 and the connection to the control leads 28 when the terminal connector 22 is in use. From FIG. 11, the base 96 contains the terminals 26 and also has an opening that includes a grommet or strain relief 27. The control leads 28 pass through the grommet or strain relief 27 and are attached to terminals 26. Resilient pad 38 reduces vibration and reduces air 16 leakage through the hole 34 in the duct 10 outside wall 32.

The embodiment of FIGS. 10, 11 and 12 is referred to as the molded flange connector. FIG. 12 shows the molded flange connector installed and with the cover 98 removed. The molded flange connector may be attached to the outside wall 32 of the duct 10 by any suitable attachment mechanism or fastener, such as sheet metal screws passing through the holes illustrated by FIGS. 10 and 11.

Figure 13:
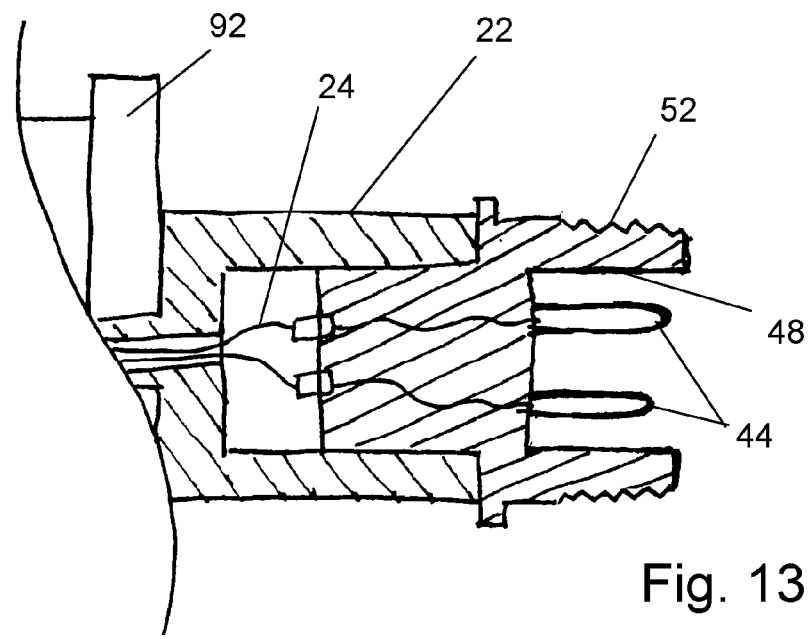
FIG. 13 is a schematic cross section of the terminal connector.
Figure 14:
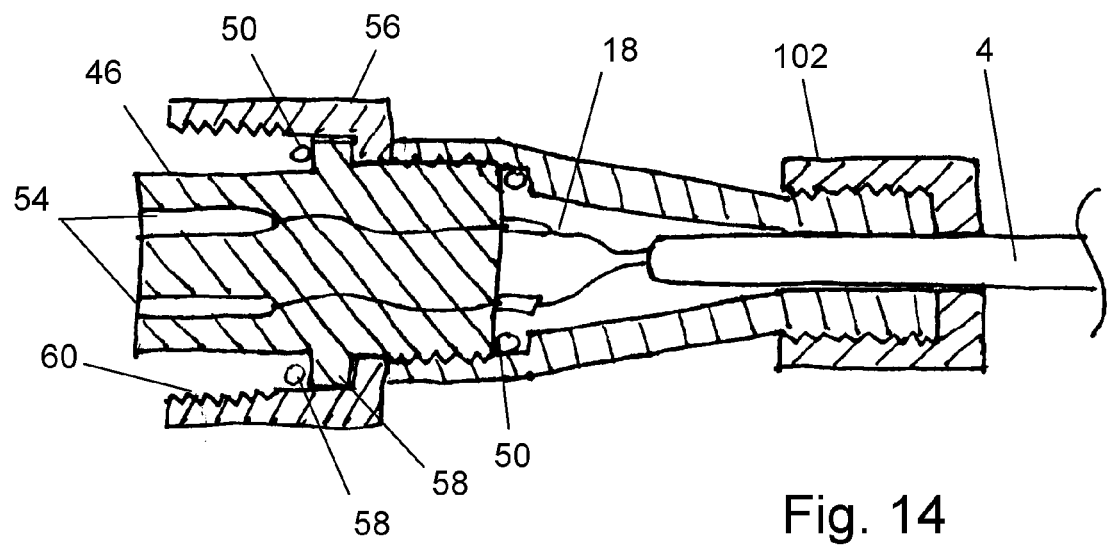
FIG. 14 is a schematic cross section of the housing connector.
Figure 15:
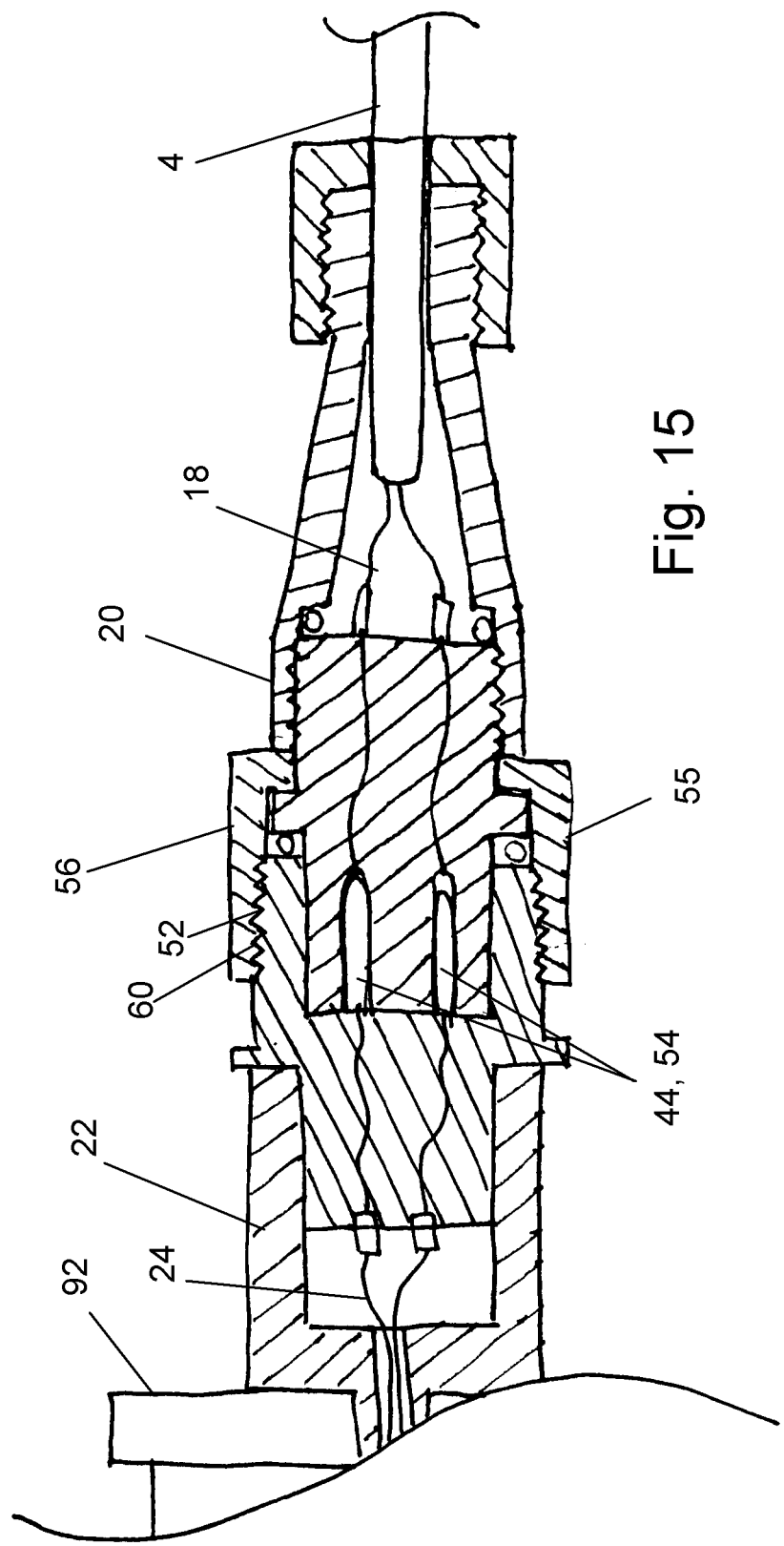
FIG. 15 is a schematic cross section of the terminal connector attached to the housing connector.

One possible construction of the terminal connector 22 and housing connector 20 and the electrical connections of the duct averaging sensor 2 are illustrated by FIGS. 13 through 16. FIG. 13 is a schematic cross section of the terminal connector 22. Conductive probes 44 are electrically connected by terminal connector leads 24 to the terminals 26. A perspective view of the probes 44 is included in FIG. 6. FIG. 14 is a schematic cross section of the housing connector 20. Housing 4 is retained to the housing connector 20 by compression fitting 102. Housing leads 18 carry the electrical signal from the sensor elements 8 and are connected to conductive apertures 54. Conductive apertures 54 are configured to engage the conductive probes 44 of the terminal connector 22, as illustrated by FIG. 15, which shows the terminal connector 22 and the housing connector 20 in engagement.

FIGS. 13-15 also show one possible mechanical connection between the housing connector 20 and the terminal connector 22. Housing connector 20 defines a male portion 46 and terminal connector 22 defines a corresponding female portion 48. The male and female portions 46, 48 are configured for sliding engagement, the orientation of which may be controlled by keys and corresponding slots. A locking nut 56 is retained on the housing connector 20 by a boss 58 and is rotatable with respect to the housing connector 20. When the male and female portions 46, 48 are in engagement, the internal threads 60 of the locking nut 56 can engage external threads 52 of the terminal connector 22, locking the housing connector 20 to the terminal connector 22. The sliding engagement of the male and female portions 48, 46 engages O-rings 50, excluding water and air from the connection between the conductive apertures 54 and the conductive probes 44. The combination of the slidable engagement and locking nut 56 provides a robust connection between the housing connector 20 and the terminal connector 22.

Any other suitable fastener 55 connecting the housing connector 20 and the terminal connector 22 is contemplated by the invention, including a bayonet connection 62, an adhesive 64, a clamp 66, a mechanical clip 68, and a threaded fastener 70 (see FIG. 7). Threaded fastener 70 may be a screw, bolt, nut, stud or any other suitable threaded fastener 70.

The housing connector 20 is shown as located at one end of the housing 4. Alternatively, the housing connector 20 may be attached to the housing 4 at a location other than the end. The housing connector 20 is selectably attachable to and detachable from a terminal connector 22.

A resilient pad 38, shown by FIG. 4, may be interposed between the outside wall 32 of the duct 10 and the terminal connector 22, junction box 6, or flange 92 to dampen vibration. The resilient pad 38 may provide an adhesive connection between the terminal connector 22, flange 92, or junction box 6 and the outside wall 32. The resilient pad 38 also serves to prevent movement of air 16 through the hole 34 either into or out of the inside 40 of the duct 10.

Figure 16:
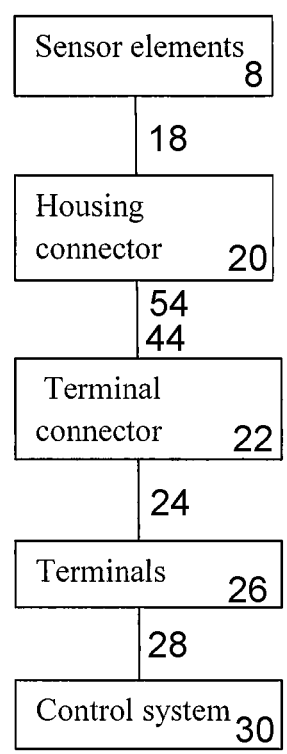
FIG. 16 is a schematic diagram of the electrical connections of the duct averaging sensor.

FIG. 16 is an electrical schematic diagram of the duct averaging sensor 2 as installed. The sensor elements 8 are connected by sensor leads 18 to the housing connector 20, which is electrically connected to the terminal connector 22 by electrically conductive apertures 54 in engagement with electrically conductive probes 44. The terminal connector 22 is electrically connected to terminals 26 of the junction box 6 by junction box leads 24. Control leads 28 electrically connect the terminals 26 to the control system 30. The duct averaging sensor 2 thus informs the control system 30 of the environmental condition of the air 16 in the duct 10 being monitored.

The sensor elements 8 may be selected to monitor any desired environmental condition within the duct 10, including at least temperature and humidity. From FIG. 2, where the monitored environmental condition is temperature, the sensor elements 8 may be, for example, thermisters 74, thermocouples 78 or resistance temperature detectors 80. Where the monitored environmental condition is humidity, the sensor elements 8 may be, for example, capacitive humidity sensors 80, resistive humidity sensors 82, or thermal conductivity humidity sensors 84. Any other sensor known in the art that is capable of sensing any desired environmental condition is contemplated by the invention.

Figure 17:
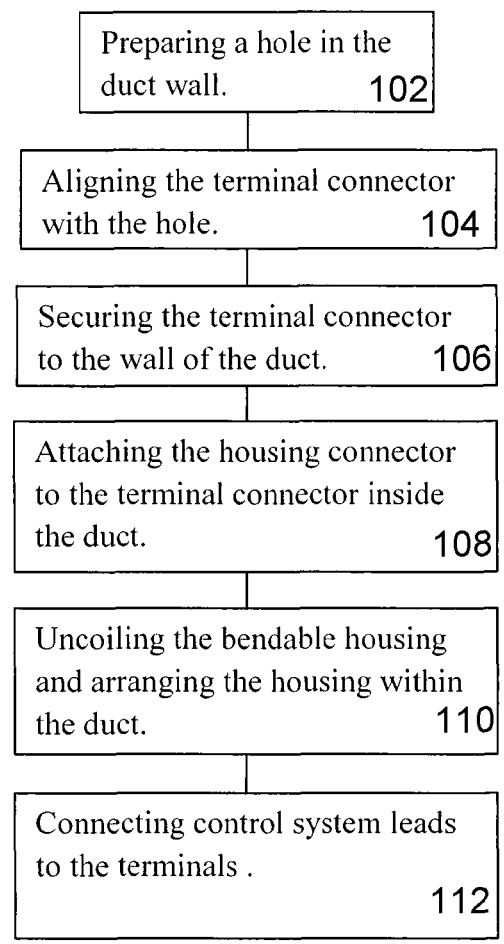
FIG. 17 is a flow chart of a method of using the duct averaging sensor.

FIG. 17 is a flow chart of a method of using the duct averaging sensor 2. In step 102 of FIG. 10, the technician prepares a hole 34 communicating through the outside wall 32 of the duct 10 at the location where monitoring of the air 16 flowing through the duct 10 is desired. The technician then aligns the terminal connector 22 with the hole 34 and attaches the terminal connector 22 to the outside wall 32, as indicated by steps 104 and 106 of FIG. 17. The technician moves to the inside 40 of the duct 10 and attaches the housing connector 20 to the terminal connector 22, thereby attaching the housing 4 to the outside wall 32 of the duct 10, as indicated by step 108 of FIG. 17. Where the housing 4 is a bendable tube 12 in a coiled condition, the technician uncoils the tube 12 and arranges the tube 12 inside 40 the duct 10 so that the sensor elements 8 are in appropriate locations within the duct 10, indicated by step 110 of FIG. 17. The technician then connects the control system leads 28 to the terminals 26, as indicated by step 112, completing installation. Alternatively, the technician may connect the control system leads 28 to the terminals 26 at the time of attaching the terminal connector 22 to the wall 32 of the duct 10 and prior to attaching the housing connector 20 to the terminal connector 22.

The duct averaging sensor 2 of the invention may be of any length 14, such as six, twelve or twenty-four feet, and may contain any desired number of sensor elements 8, such as nine sensor elements 8. In addition to a coiled housing 4, the duct averaging sensor 2 may utilize a straight housing 4, such as a housing 4 composed of a stainless steel tube.

LIST OF NUMBERED ELEMENTS

The following elements having the following numbers appear in the drawings and specification.
duct averaging sensor 2
housing 4
junction box 6
sensor elements 8
duct 10
tube 12
length 14
air 16
sensor leads 18
housing connector 20
terminal connector 22
terminal leads 24
terminal 26
strain relief 27
control lead 28
opening (hole) for control leads 29
control system 30
outside wall 32
hole in the duct wall 34
resilient pad 38
inside of the duct 40
opening in the junction box to receive terminal connector 42
two conductive probes 44
male portion 46
female portion 48
O-ring 50
external threads 52 two conductive apertures 54
fastener 55
locking nut 56
boss 58
internal threads 60
bayonet connection 62
adhesive 64
clamp 66
mechanical clip 68
threaded fastener 70
thermister 74
thermocouple 76
resistance temperature detector 78
capacitive humidity sensor 80
resistive humidity sensor 82
thermal conductivity humidity sensor 84
galvanized junction box 86
galvanized enclosure connector 88
molded flange connector 90
flange 92
knock-out opening 94
base 96
cover 98
enclosure 100
compression fitting 102
nut 104
screw 106

We claim:

1. A duct averaging sensor, the duct averaging sensor comprising:
   a. a plurality of sensor elements, each of said sensor elements being configured to detect an environmental condition;
   b. a housing, said plurality of sensor elements being disposed within said housing, said housing having a housing length;
   c. a housing connector, said housing connector being attached to said housing, said housing connector being electrically connected to said sensor elements;
   d. a terminal connector, said terminal connector being selectably attachable to and detachable from said housing connector, said terminal connector being selectably attachable to an outside surface of a duct, said terminal connector being configured to penetrate a hole defined by said outside surface of said duct, said terminal connector defining a terminal connector length within said duct when said terminal connector is penetrating said hole, said housing length being greater than said terminal connector length, said terminal connector and said housing connector being in electrical communication when said terminal connector and said housing connector are attached; and,
   e. a terminal, said terminal being electrically connected to said terminal connector, said terminal being configured for connection to a control system, said terminal being electrically connected to said plurality of sensor elements when said terminal connector and said housing connector are attached.

2. The duct averaging sensor of claim 1 wherein said terminal connector is a terminal flange connector having a flange, said flange being configured for connection to said outside surface of a wall of said duct, said terminal being disposed outside of said duct when said flange is connected to said outside surface, said housing being disposed inside of said duct when said flange is connected to said outside surface and said housing connector is attached to said terminal flange connector.

3. The duct averaging sensor of claim 1 wherein said terminal connector having a configuration to be attached to a junction box.

4. The duct averaging sensor of claim 3 wherein said configuration for said terminal connector to be attached to said junction box comprising: said terminal connector being sized to communicate through a knock-out opening in said junction box.

5. The duct averaging sensor of claim 1 wherein a one of said terminal connector and said housing connector defines a male portion and the other of said terminal connector and said housing connector defines a female portion, said male portion and said female portion being configured for a slidable engagement.

6. The duct averaging sensor of claim 5, the apparatus further comprising: two conductive apertures disposed on said male portion and two conductive probes disposed on said female portion, each of said probes being in electrical communication with a one of said apertures when said housing connector and said terminal connector are attached.

7. The duct averaging sensor of claim 5 wherein said housing connector is selectably attachable to said terminal connector by a fastener, said fastener being selected from a list consisting of: a locking nut, a bayonet connection, an adhesive, a clamp, a mechanical clip, and a threaded fastener.

8. The duct averaging sensor of claim 1 wherein said environmental condition is temperature.

9. The duct averaging sensor of claim 8 wherein each said sensor element is selected from a list consisting of a thermister, a thermocouple and a resistance temperature detector.

10. The duct averaging sensor of claim 1 wherein said environmental condition is humidity.

11. The duct averaging sensor of claim 10 wherein each said sensor element is selected from a list consisting of a capacitive humidity sensor, a resistive humidity sensor, and a thermal conductivity humidity sensor.

12. The duct averaging sensor of claim 1 wherein said housing connector and said terminal connector are configured for selectable attachment and detachment by a person located on an inside of said duct when said terminal connector is attached to said outside surface of said duct.

13. The duct averaging sensor of claim 1 wherein said housing is not configured to pass through said terminal connector from an outside of said duct to an inside of said duct when said terminal connector is attached to said outside surface of said duct and penetrating said hole.

14. The duct averaging sensor of claim 1 wherein said housing is a bendable tube.

15. The duct averaging sensor of claim 14 wherein said bendable tube is coiled.

16. A duct averaging sensor, the duct averaging sensor comprising:
   a. a plurality of sensor elements, each of said sensor elements being configured to detect an environmental condition;
   b. a housing, said plurality of sensor elements being disposed within said housing;
   c. a housing connector, said housing connector being attached to said housing, said housing connector being electrically connected to said sensor elements;
   d. a terminal connector, said terminal connector being selectably attachable to and detachable from said housing connector, said terminal connector and said housing connector being in electrical communication when said terminal connector and said housing connector are attached; and e. a terminal, said terminal being electrically connected to said terminal connector, said terminal being configured for connection to a control system, said terminal being electrically connected to said plurality of sensor elements when said terminal connector and said housing connector are attached, a one of said terminal connector and said housing connector defining a male portion and the other of said terminal connector and said housing connector defining a female portion, said male portion and said female portion being configured for a slidable engagement wherein said housing connector is selectably attachable to said terminal connector by a fastener, said fastener being a locking nut attached to said housing connector, said locking nut having internal threads, said internal threads of said locking nut being configured to selectably engage corresponding external threads of said terminal connector.

17. A duct averaging sensor, the duct averaging sensor comprising:
   a. a plurality of sensor elements, each of said sensor elements being configured to detect an environmental condition;
   b. a housing, said plurality of sensor elements being disposed within said housing;
   c. a housing connector, said housing connector being attached to said housing, said housing connector being electrically connected to said sensor elements;
   d. a terminal connector, said terminal connector being selectably attachable to and detachable from said housing connector, said terminal connector and said housing connector being in electrical communication when said terminal connector and said housing connector are attached; and
   e. a terminal, said terminal being electrically connected to said terminal connector, said terminal being configured for connection to a control system, said terminal being electrically connected to said plurality of sensor elements when said terminal connector and said housing connector are attached, a one of said terminal connector and said housing connector defining a male portion and the other of said terminal connector and said housing connector defining a female portion, said male portion and said female portion being configured for a slidable engagement wherein said housing connector and said terminal connector have a configuration to exclude water from said electrical connectors when said housing connector and said terminal connector are attached, said configuration to exclude water comprising: an O-ring disposed between said housing connector and said terminal connector.

18. A method of installing a duct averaging sensor, the method comprising:
   a. providing a duct averaging sensor having a housing containing a plurality of sensor elements, said duct averaging sensor also having a terminal connector, said housing being selectably attachable to said terminal connector, said terminal connector being electrically connected to a terminal;
   b. aligning said terminal connector with a hole communicating through an outside wall of a duct;
   c. installing said terminal connector to an outside surface of said duct;
   d. disposing said housing inside said duct without passing said housing through said hole;
   e. attaching said housing to said terminal connector after said step of disposing said housing inside said duct.

19. The method of claim 18 wherein said housing includes a housing connector attached to said housing, said housing connector being configured for a releasable connection to said terminal connector, said step of attaching said housing to said terminal connector comprising: attaching said housing connector to said terminal connector wherein a one of said terminal connector and said housing connector extend through said hole when said terminal connector and said housing connector are attached.

20. The method of claim 19 wherein said housing connector and said terminal connector are selectably detachable.

21. The method of claim 19 wherein said step of attaching said housing connector to said terminal connector is selected from a list consisting of: threading a locking nut, engaging a bayonet connection, joining the housing and terminal connectors using an adhesive, joining the housing and terminal connectors using a mechanical clip, and joining the housing and the terminal connectors using a threaded fastener.

22. The method of claim 18 wherein said step of installing said terminal connector to said outside surface of said duct comprises:
   a. attaching said terminal connector to a junction box so that said terminal is inside said junction box; and
   b. attaching said junction box to said outside surface of said duct.

23. The method of claim 22 wherein said step of attaching said terminal connector to said junction box comprises:
   a. penetrating a knock-out opening defined by said junction box with said terminal connector;
   b. securing said terminal connector in said knock-out opening.

24. The method of claim 18 wherein said terminal is disposed within a junction box, said junction box defining an opening, said terminal connector penetrating said opening, said step of installing said terminal connector to said outside surface of said duct comprising:
   a. preparing said hole in said an outside wall of said duct, said outside wall defining said outside surface;
   b. inserting said terminal connector into said hole in said duct from an outside of said duct; and
   c. securing said junction box to said outside surface of said duct.

25. A method of installing a duct averaging sensor, the method comprising:
   a. providing a duct averaging sensor having a housing containing a plurality of sensor elements, said duct averaging sensor also having a terminal connector, said housing being selectably attachable to said terminal connector, said terminal connector being electrically connected to a terminal;
   b. installing said terminal connector to an outside wall of a duct;
   c. disposing said housing inside said duct;
   d. attaching said housing to said terminal connector after said step of disposing said housing inside said duct, wherein said housing is a bendable tube having a length, said bendable tube containing said plurality of sensor elements distributed along said length of said tube, said tube being initially coiled, the method further comprising: uncoiling said tube after said step of attaching said housing to said terminal connector.

26. A method of installing a duct averaging sensor, the method comprising:
   a. providing a duct averaging sensor having a housing containing a plurality of sensor elements, said duct averaging sensor also having a terminal connector, said housing being selectably attachable to said terminal connector, said terminal connector being electrically connected to a terminal;
b. installing said terminal connector to an outside wall of a duct;
c. disposing said housing inside said duct;
d. attaching said housing to said terminal connector after said step of disposing said housing inside said duct, wherein said housing is a bendable tube having a length, said bendable tube containing said plurality of sensor elements distributed along said length of said tube, said tube being initially coiled, the method further comprising: uncoiling said tube before said step of attaching said housing to said terminal connector.

27. A duct averaging sensor, the duct averaging sensor comprising:
a. a plurality of sensor elements, each of said sensor elements being configured to detect an environmental condition;
b. a housing, said plurality of sensor elements being disposed within said housing;
c. a housing connector, said housing connector being attached to said housing, said housing connector being electrically connected to said sensor elements;
d. a terminal connector, said terminal connector being selectably attachable to and detachable from said housing connector, said terminal connector being configured for attachment to an outside surface of a duct, said housing connector being configured to penetrate a hole defined by said outside surface of said duct and to engage said terminal connector, said terminal connector defining a terminal connector length, said housing length being greater than said terminal connector length, said terminal connector and said housing connector being in electrical communication when said terminal connector and said housing connector are attached; and
e. a terminal, said terminal being electrically connected to said terminal connector, said terminal being configured for connection to a control system, said terminal being electrically connected to said plurality of sensor elements when said terminal connector and said housing connector are attached.

28. The duct averaging sensor of claim 27 wherein said housing is configured not to pass through said terminal connector from an outside of said duct to an inside of said duct when said terminal connector is attached to said outside surface of said duct.

29. The duct averaging sensor of claim 27 wherein said housing is a bendable tube.

30. The duct averaging sensor of claim 29 wherein said bendable tube is coiled.

* * * * *